(12) United States Patent
Feilbogen et al.

(10) Patent No.: US 8,078,511 B2
(45) Date of Patent: Dec. 13, 2011

(54) METHOD AND SYSTEM FOR FOREIGN EXCHANGE PRICE PROCUREMENT AND AUTOMATED HEDGING

(75) Inventors: Robert J. Feilbogen, Chappaqua, NY (US); Paul Varnish, London (GB)

(73) Assignee: American International Group, Inc., New York, NY (US)

( * ) Notice: Subject to any disclaimer, the term of this patent is extended or adjusted under 35 U.S.C. 154(b) by 1387 days.

(21) Appl. No.: 09/871,569

(22) Filed: May 31, 2001

(65) Prior Publication Data

US 2002/0016762 A1 Feb. 7, 2002

Related U.S. Application Data

(60) Provisional application No. 60/208,137, filed on May 31, 2000, provisional application No. 60/208,547, filed on Jun. 1, 2000.

(51) Int. Cl.
*G06Q 40/00* (2006.01)
(52) U.S. Cl. ......................................................... 705/35
(58) Field of Classification Search ........................ None
See application file for complete search history.

(56) References Cited

U.S. PATENT DOCUMENTS

| 5,620,182 | A | | 4/1997 | Rossides | |
|---|---|---|---|---|---|
| 5,704,045 | A | | 12/1997 | King et al. | |
| 5,884,274 | A | | 3/1999 | Walker et al. | |
| 5,897,621 | A | * | 4/1999 | Boesch et al. | 705/26 |
| 6,460,020 | B1 | * | 10/2002 | Pool et al. | 705/26 |
| 7,024,383 | B1 | * | 4/2006 | Mancini et al. | 705/35 |

FOREIGN PATENT DOCUMENTS

| EP | 0949596 A2 | 10/1999 |
|---|---|---|
| WO | 97/48078 A | 12/1997 |
| WO | 99/24921 | 5/1999 |

* cited by examiner

*Primary Examiner* — Jason M Borlinghaus
(74) *Attorney, Agent, or Firm* — Leydig, Voit & Mayer. Ltd.

(57) ABSTRACT

In the present invention, a hedging engine processor and method monitors business transactions to provide foreign currency exchange hedging instructions and to provide foreign currency price information for goods of commerce. The hedging engine receives business transaction information that relate to purchases or sales of goods by a customer, receives hedging rules, that define rules to exchange a first type of currency to a second type of currency, and receives pricing rules, that define rules to update public foreign currency prices of the goods. The engine also generates public price information to provide foreign currency prices of the goods, based on the pricing rules, and generates hedging instruction information to provide instructions on whether to exchange from the first type of currency to the second type of currency, based on the hedging rules.

35 Claims, 14 Drawing Sheets

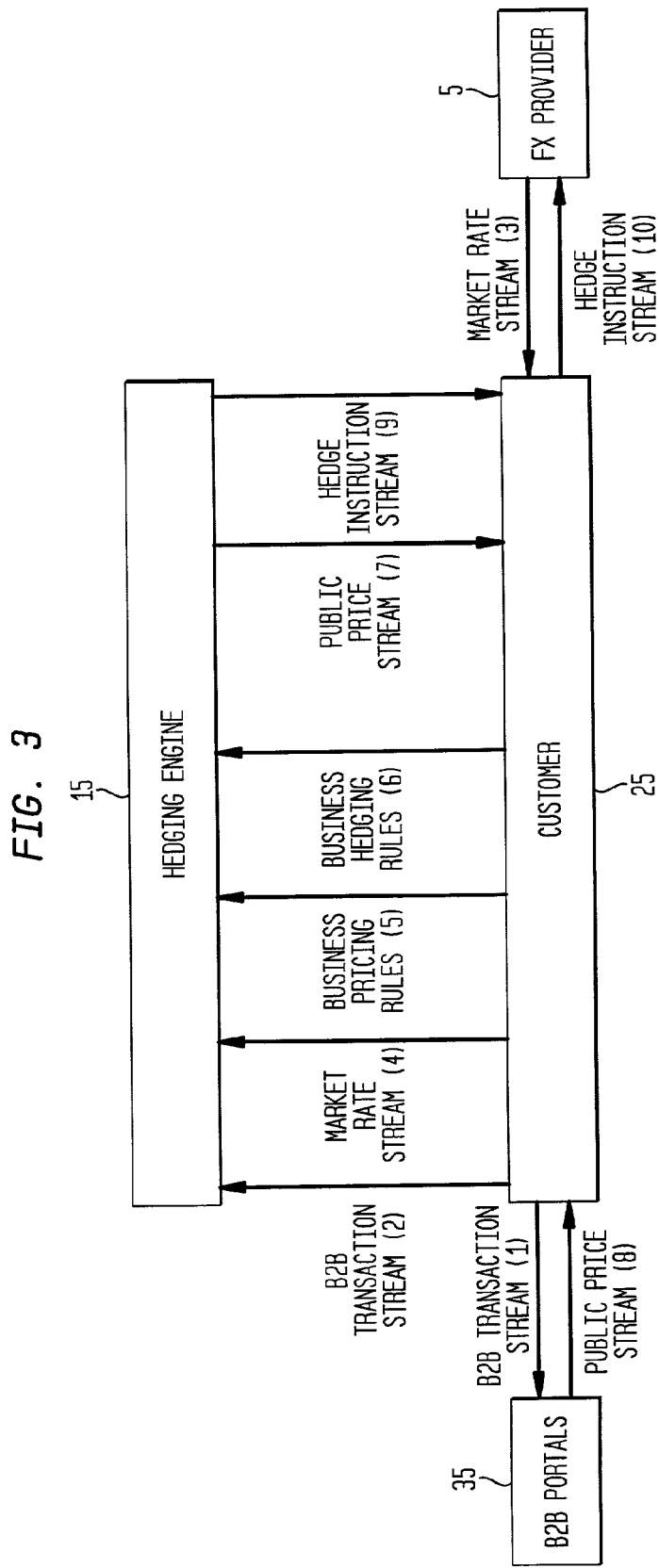

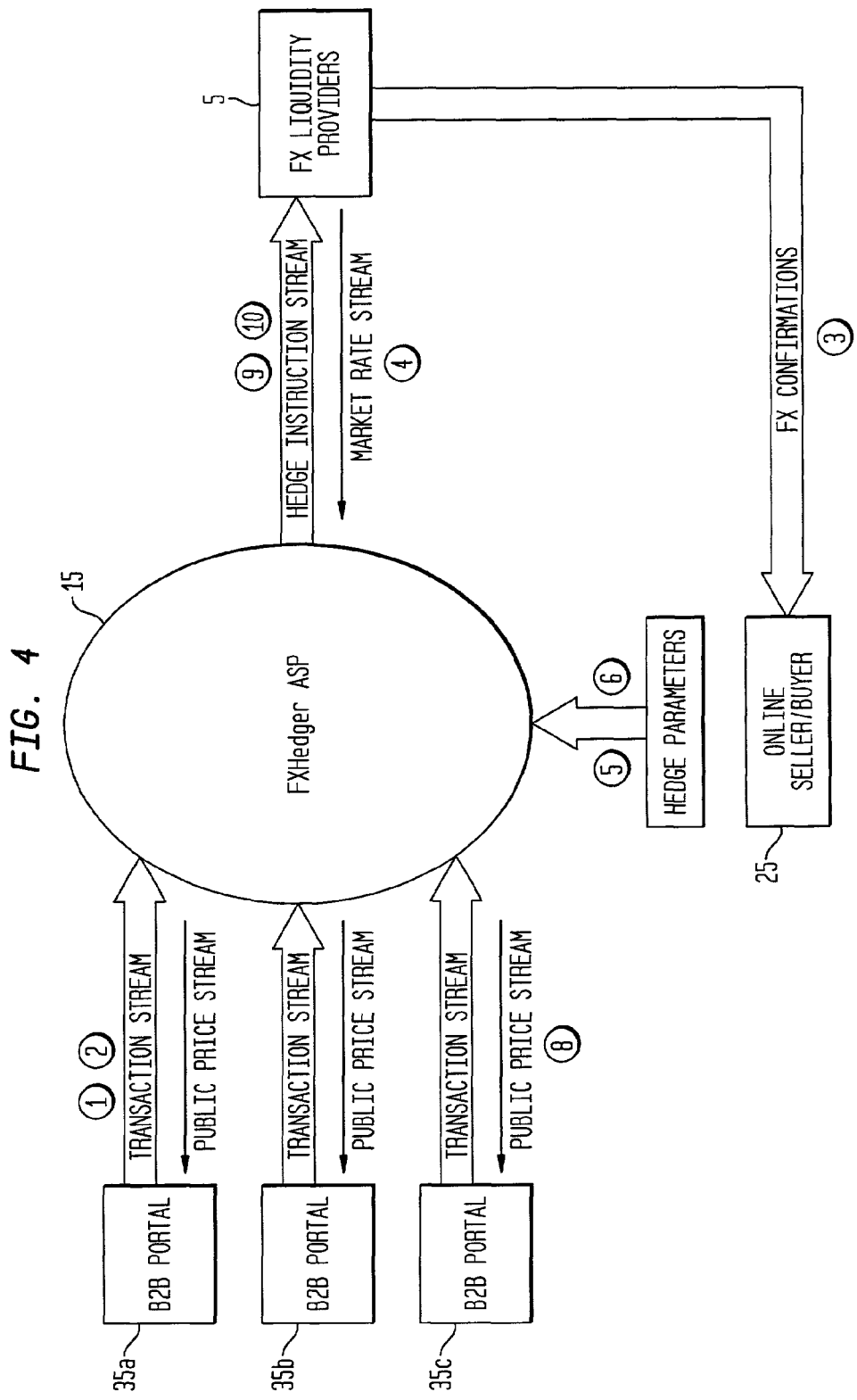

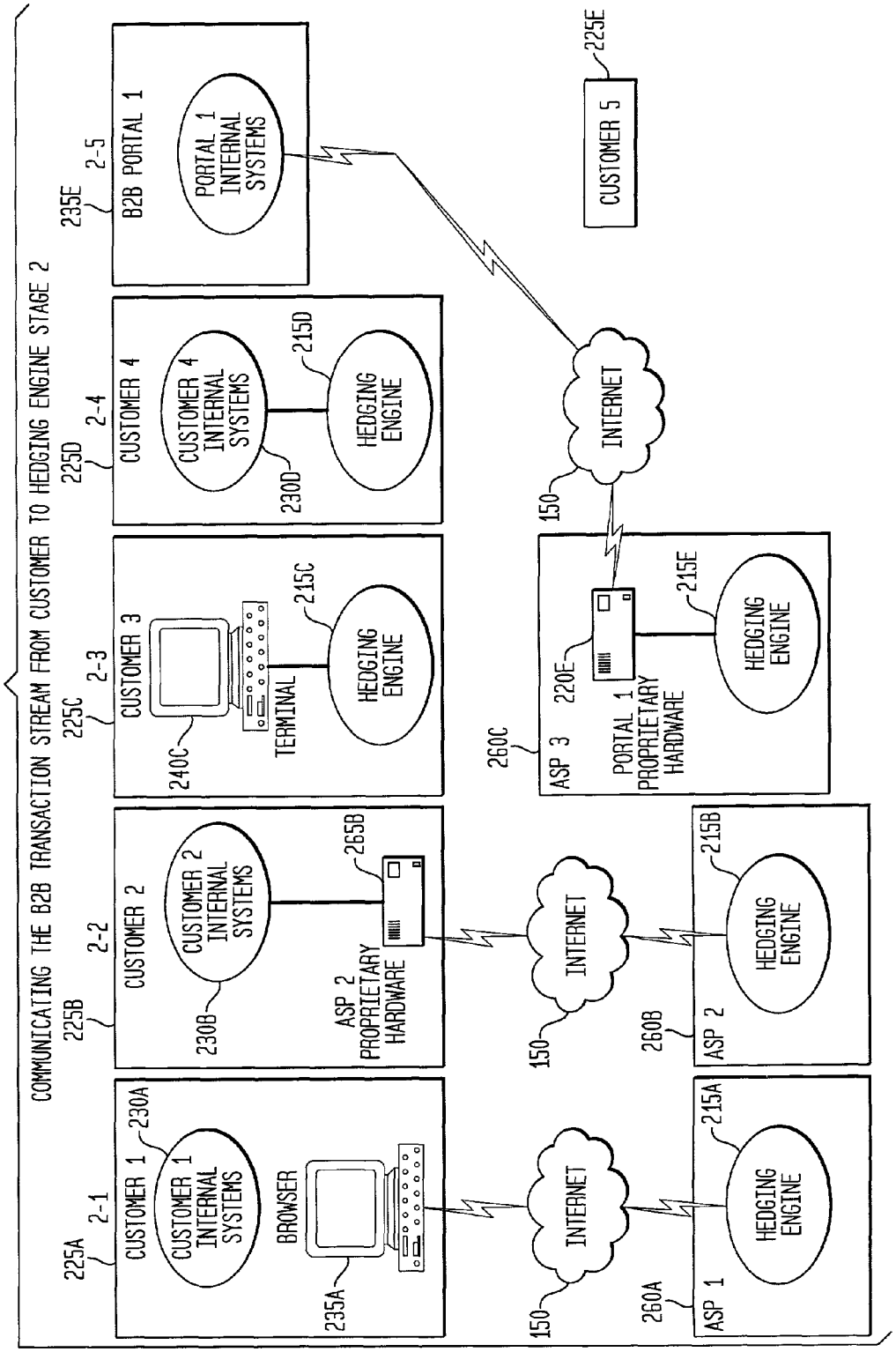

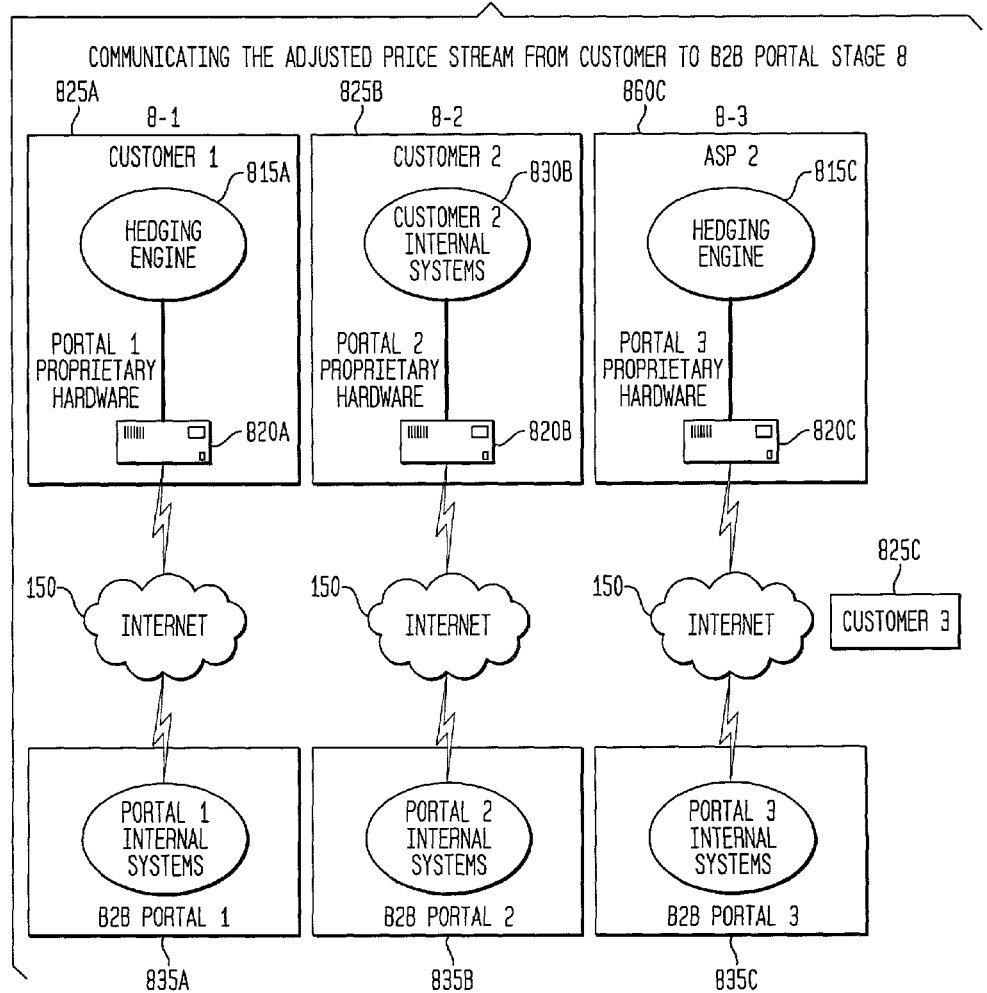

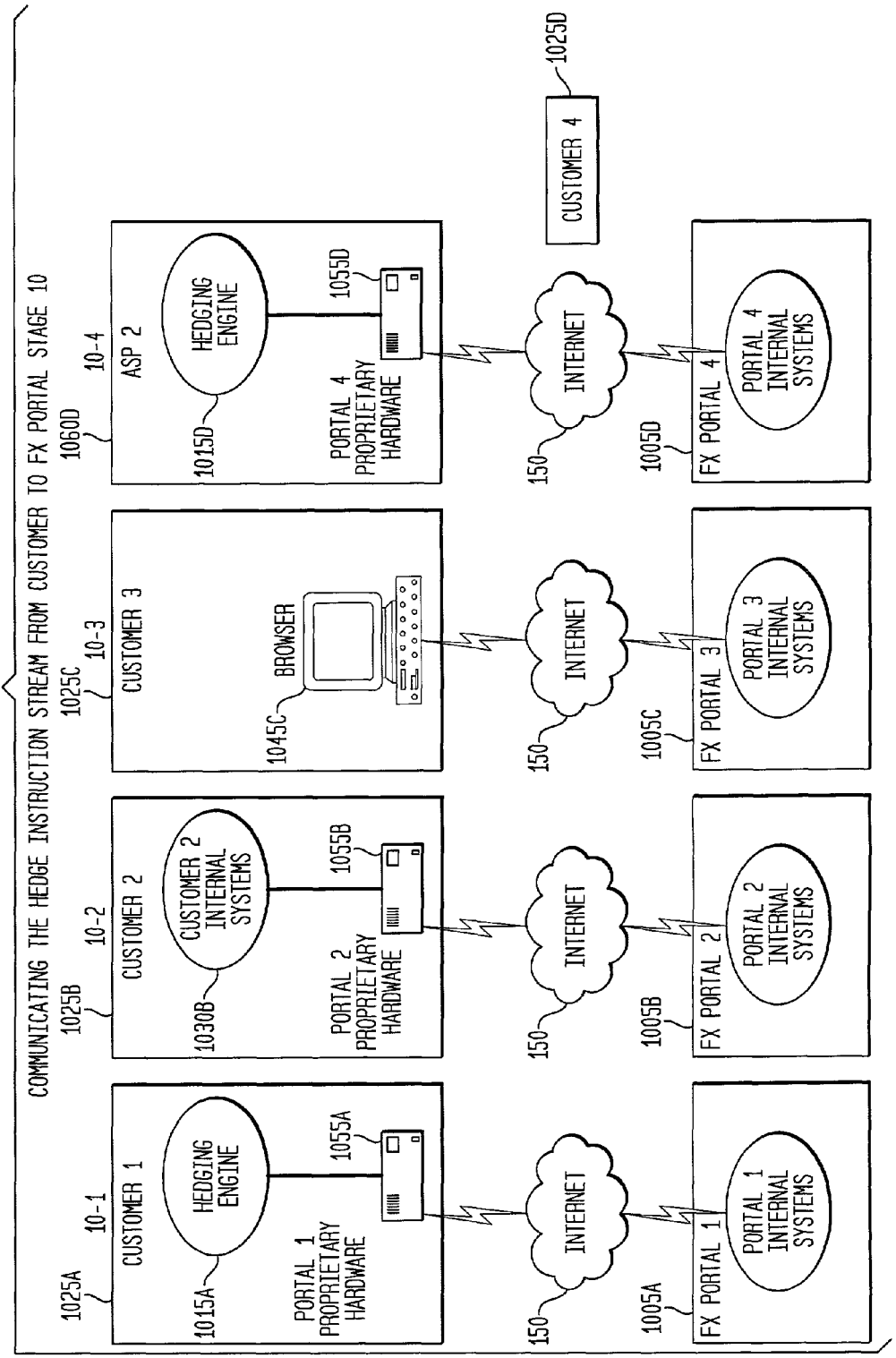

METHOD AND SYSTEM FOR FOREIGN EXCHANGE PRICE PROCUREMENT AND AUTOMATED HEDGING

RELATED APPLICATION

This application is based upon and claims the benefit of U.S. provisional application Ser. No. 60/208,137, filed on May 31, 2000 for Robert J. Feilbogen, and Ser. No. 60/208, 547, filed on Jun. 1, 2000 for Robert J. Feilbogen, all entitled "METHOD AND SYSTEM FOR FOREIGN EXCHANGE PRICE PROCUREMENT AND AUTOMATED HEDGING." The contents of these provisional applications are fully incorporated herein by reference.

FIELD OF THE INVENTION

The present invention relates to a method and processor engine for monitoring business transactions and for providing foreign currency exchange hedging instructions and foreign currency price information for goods of commerce. More specifically, the present invention relates to a method and processor engine for monitoring business transactions of sales and purchases of goods by a customer and for providing foreign currency exchange hedging instructions, based on received hedging rules, and foreign currency price information, based on received pricing rules, for goods of commerce.

BACKGROUND OF THE INVENTION

With the recent prevalence of the Internet, buying and selling goods, services, and financial instruments across international boarders have become increasingly common. Such buying and selling is typically referred to as conducting "e-commerce." In practice, e-commerce (electronic commerce) and a newer term, e-business, are often used interchangably. E-commerce can be divided into several categories, including "e-tailing" and business-to-business (B2B) buying and selling.

For example, e-tailing (or "virtual storefronts") are located on World Wide Web sites along with online catalogs. Many virtual storefronts can form a "virtual mall." As a place for direct retail shopping, with its 24-hour availability, a global reach, the ability to interact and provide custom information and ordering, and multimedia prospects, the Web is rapidly becoming a multibillion dollar source of revenue for the world's businesses. For example, as early as the middle of 1997, Dell Computers reported orders of a million dollars a day. By early 1999, projected e-commerce revenues for business were in the billions of dollars and the stocks of companies deemed most adept at e-commerce were skyrocketing. Although many so-called "dotcom" retailers disappeared in the economic shakeout of 2000, Web retailing at sites such as Yahoo.com, Amazon.com, CDNow.com, and Compudata-Online.com continues to grow.

In addition, thousands of companies that sell products to other companies have discovered that the Web provides not only a 24-hour-a-day showcase for their products but a quick way to reach the right people in a company for more information. This is known as business-to-business buying and selling.

As a result of global e-commerce, buyers and sellers often transact business between countries. Accordingly, foreign currency exchange comes into play. However, the value of currency (the currency rate) for each country continuously varies, so there is never a set foreign exchange rate. As a simple example, a purchaser may be from the U.S., while a vendor may be from Europe. If the vendor accepts U.S. currency, the vendor will have to be concerned with the fluctuation of the U.S. dollar vis-á-vis the Euro. More generally, a vendor will need to exchange received foreign currency to the currency that the vendor uses in his accounting, regardless of the country where he resides. Of course, the country of the vendor typically coincides with the currency used in his accounting.

Consider the case where Yahoo! Italy posts prices in Euros, presumably because the users of Yahoo! Italy reside in Italy or an European Community country. To the extent that another currency is displayed (say U.S. dollars), the conversion rates will likely not represent current market rates. Assume that the current foreign exchange rate for the Euro is $0.89 U.S.=€1 Euro. However, a Yahoo! tee-shirt is being sold for either $15 U.S. or 13.55 Euro. This implies that $1.107=€1 Euro, which will be assumed to have been the exchange rate when Yahoo! originally posted its price for the subject tee-shirts. The proper price of the tee-shirt, given current rate, would be either $12.06 and €13.55, or $15.00 and €16.85. However, the exchange rate used by Yahoo! is stale, as the Euro lost value to the U.S. dollar.

As illustrated above, vendors who sell goods and services in a variety of currencies are vulnerable to stale foreign exchange rates. If Yahoo! sells 100,000 tee-shirts in Europe at €13.55 Euro, and exchanges the Euro into U.S. dollars at the market exchange rate, then they will have incurred a loss of $3 per tee shirt ($300,000 total) due to stale foreign exchange rates. Accordingly, to limit its foreign exchange exposure, the vendor may periodically sell its foreign currency in exchange for its own currency. This is referred to as foreign exchange "hedging." When and how much to foreign currency to exchange at any time may be decided by the vendor's hedging policies or rules.

To facilitate foreign exchange transactions, vendors and purchasers create credit relationships with one or more foreign exchange (FX) rate providers. A FX rate provider can give the purchaser or vendor an update of the current exchange rate, and conduct the exchange transaction. Generally, vendors and purchasers trade in foreign exchange with said rate providers over the telephone or over the Internet.

Vendors have a number of different approaches towards managing and hedging their foreign exchange exposure including, but not limited to: individual transaction hedging; aggregated transaction hedging; and average or baseline rate hedging. Of course, hedging may include any combination of the above, as well as more sophisticated methods of hedging.

Individual transaction hedging is simply hedging on a transaction-per-transaction basis. Aggregated transaction hedging is based on time intervals (i.e. daily, weekly, monthly, etc.) or based on a notional amount (e.g., hedge every $100,000 worth of transactions). Average or baseline rate hedging allows the vendor to net its foreign exchange risks across revenue and expense streams. In this case, the vendor's accounting personnel (i.e., its treasury group) will manage the foreign exchange exposure and hedge the net risk.

However, conventionally the hedging transactions are conducted in separate mediums from the underlying purchase or sale transactions. In other words, purchasers and sellers of the goods and services transact in the foreign currency and subsequently hedge their foreign exchange exposure separately. Alternatively, they may use services, such as those provided by credit cards, that automatically convert the currency for the purchaser.

There are many shortcomings in the current landscape of global e-commerce. For example, in some instances the purchasers do not have access to all vendors because of the above described barriers related to foreign currency exchange. In other instances, the purchasers can only transact in foreign currency and have no means, or at best inefficient means, available to them for hedging. Credit Card purchases are a perfect example. The purchaser is not made aware of the foreign exchange rate, i.e., the cost of the goods in their "home" currency, until after the transaction has been completed.

Whether hedging occurs on a transaction-by-transaction basis, aggregate basis, or by any other means, given the technology available today, the only solution is to transact the foreign exchange hedge independently from the underlying purchase or sale of goods. Separate scripts need to be written in order to automate the feed, of the underlying transaction details and of the foreign exchange transaction details, into the operational systems that rely on this information (e.g., accounting systems and inventory systems).

FIG. 1 shows a schematic representing an example of an e-commerce transaction and an independent foreign exchange hedging transaction. Assume for FIG. 1 that S (a seller of widgets) operates in currency $. B (a buyer) operates in currency €. B goes to S's website to buy 1000 widgets. B only has a € bank account. S has a preferred FX rate provider 5 which offers €/$ trading capability. S also has a "nostro" bank 58, where S holds nostro accounts in both € and $. A nostro account is a foreign currency current account that is used to receive and pay currency assets and liabilities potentially denominated in a currency other than that of the country in which the bank is resident. Assume at the time of the transaction, the foreign exchange is €1.1=$1.

In Step 10, S's treasury department 18 monitors the foreign exchange market and the transaction flow from its website 28 independently from each other. In Step 20, the treasury department 18 intermittently updates the foreign selling price of goods on S's website 28, based on the market exchange rate. In Step 30, S displays the prices of his widgets in €, which B views on his computer 38. In Step 40, B purchases 1000 widgets. The transaction record is passed to the treasury department 18 at Step 50. In Step 60, B instructs his bank 48 to pay €1,100 to S's bank 58. B's bank 48 pays €1,100 to S's nostro bank 58 at Step 70. At this point, this transaction has been processed and aggregated with past transactions. The treasury department decides if and when a hedging foreign exchange transaction is required. If they decide to execute a foreign exchange transaction, Steps 80 through 110 occur as follows.

In Step 80, an instruction is sent from the treasury department 18 to S's chosen FX rate provider 5. The rate provider 5 then executes a foreign exchange transaction with S's nostro bank 58. Specifically, S's € €account at nostro bank 58 pays €1,100 to the rate provider 5 at Step 90. In Step 100, S's chosen rate provider 5 pays $1,000 to S's $ account at nostro bank 58. Lastly, in Step 110, an FX confirmation is sent to S's operations department 68.

One problem with the above transaction is that the seller's treasury department may not be disciplined, competent or efficient enough to accurately, and in a timely fashion, reflect changes in the FX market rates. Further, risks also stem from the loose, non-automated coupling of e-commerce transactions to the corresponding FX hedges. Business rules concerning hedge criteria are applied with a significant manual effort. This often leads to errors and may encourage intentional misapplication of the seller's business rules.

SUMMARY OF THE INVENTION

The present invention is directed to a hedging engine processor and method for monitoring business transactions to provide foreign currency exchange hedging instructions and to provide foreign currency price information for goods of commerce. The hedging engine receives business transaction information that relate to purchases or sales of goods by a customer. A customer may be defined, e.g., as any company, business, or individual who buys or sells in more than one currency.

The hedging engine also receives hedging rules, that define rules to exchange a first type of currency to a second type of currency, and receives pricing rules, that define rules to update public foreign currency prices of the goods. Further, the hedging engine generates such public price information to provide foreign currency prices of the goods, based on the pricing rules, and generates hedging instruction information to provide instructions on whether to exchange from the first type of currency to the second type of currency, based on the hedging rules.

As an aspect of this embodiment, the transaction information is received via transaction data streams, the public price information is generated as public price data streams, and the hedging instruction information is generated as hedging instruction data streams.

In another embodiment, the engine receives market rate information having current market foreign exchange rates, including rates for exchanging the first type of currency to the second type of currency, and vice-versa. As an aspect of this embodiment, the public price information is further based on the received market rate information. As a further aspect, the market rate information is received via at least one market rate data stream and is received from the foreign exchange (FX) rate provider of the customer.

As an additional aspect, the pricing rules define when to update the foreign currency prices of the goods. For example, updates may occur when the current market rate deviates from the market rate information varies by at least a first predetermined amount or percent, when the rate implicit in the public price information deviates from the current market rate by at least a second predetermined amount or percent, after the expiration of a predetermined time interval (such as every week, month, etc.), and when manually requested. In addition, the pricing rules further define an updated foreign currency price of the goods. The updated price may be based on either the actual current market rate or the actual current market rate adjusted by a predetermined amount. Of course, the updated price may be manually entered as well.

In another aspect, the hedging rules further define when to exchange the first and second types of currency. For example, this may occur when the current market rate deviate from the market rate information varies by at least a first predetermined percent, at the expiration of a predetermined time interval, after a predetermined amount of units of the goods are sold or purchased, after a predetermined amount of currency is received from sales or due from purchases of the goods, and when manually requested. In addition, the hedging rules further define the amount of currency to exchange between the first and second types of currency. The amount may be based on either a total accumulated revenue or deficit of the first type of currency or a predetermined percent of the total.

As yet an additional aspect, the public price information and the hedging instruction information may be generated in a computerized system. The computerized system may be configured within a local network or stand-alone computer of the customer. Further, the computerized system may be configured within an application service provider, remote from the customer.

In a further embodiment of the invention, the hedging instruction data streams are forwarded to a FX rate provider of the customer. The foreign exchange bank then exchanges the currency of the first type to currency of the second type based on the received hedging instruction data streams. As a further aspect, the transaction data stream is received from a business-to-business (B2B) portal, wherein said B2B portal is a medium to allow said customer to buy and sell said goods.

In an additional embodiment, the hedge instruction data streams and the public price data streams are forwarded as an electronic ticket to the customer, to the FX rate provider, or to both.

It is an object of the invention to overcome the deficiencies of the prior art by providing a hedging engine processor that generates prices of goods and services, in any currency, using the foreign exchange rates from a selected FX rate provider.

It is a further object of the invention to provide a hedging engine processor that provides automated hedging instructions regarding a customer's foreign exchange exposure.

It is another object of the invention to provide a hedging engine processor that creates an electronic ticket capturing the details pertaining to the foreign exchange transaction. This enables straight-through-processing (STP).

It is an additional object of the invention to provide a hedging engine processor that creates an electronic feed, using the same format as the electronic ticket (e.g., XML), to capture the details pertaining to the underlying transaction in order to achieve STP. Accordingly, the number of scripts that need to be written, to all interested entities, to capture transaction information are minimized.

It is a further object of the invention to provide a hedging engine processor that provides an application program interface (API) which will accept streaming data of foreign exchange prices from a FX rate provider at variable intervals.

As yet an additional advantage, a clearing or prime broker type relationship can be implemented to streamline the process and to allow a customer to receive FX rates from multiple sources with one single master trading agreement with their clearing house.

As yet a further advantage, the clearing mechanism of the clearing house may provide all of the back-office settlement processes via the received electronic tickets.

Such objects and advantages listed above are merely illustrative and not exhaustive. Further, these and other features and advantages of the present invention will become more apparent from the accompanying drawings and the following detailed description.

BRIEF DESCRIPTION OF THE DRAWINGS

The following detailed description, given by way of example and not intended to limit the present invention solely thereto, will best be understood in conjunction with the accompanying drawings, where similar elements will be represented by the same reference symbols, in which:

FIG. 3 schematically illustrates a further embodiment of an automated e-commerce and hedging transaction, in accordance with the present invention; hedging transaction having an ASP infrastructure, in accordance with the present invention;

FIGS. 5A, 5B, 5C, 5D, 5E, 5F, 5G, 5H, and 5I schematically illustrate the stages in FIGS. 3 and 4, in accordance with the present invention.

DETAILED DESCRIPTION OF PREFERRED EMBODIMENTS

In an embodiment of the invention, a hedging engine is implemented in a customer's computer system or on a remote application service provider's (ASP) server. Illustratively, the hedging engine is software, written, e.g., in JAVA or C++. However, it may be implemented as hardware or firmware as well. In general, the hedging engine monitors business transactions of the customer (a buyer or seller), and generates appropriate foreign exchange hedging instructions, based on customer-controlled parameters, that are routed to a bank or FX rate provider, as determined by the customer. Illustratively, a "customer" is defined as an individual or business that buys or sells in more than one currency. Thus, a customer may be a purchaser or a vendor. It should be noted that the invention is not limited to hedging foreign exchange exposure. Instead, the hedging engine is applicable to other financial paradigms.

Figure 1:
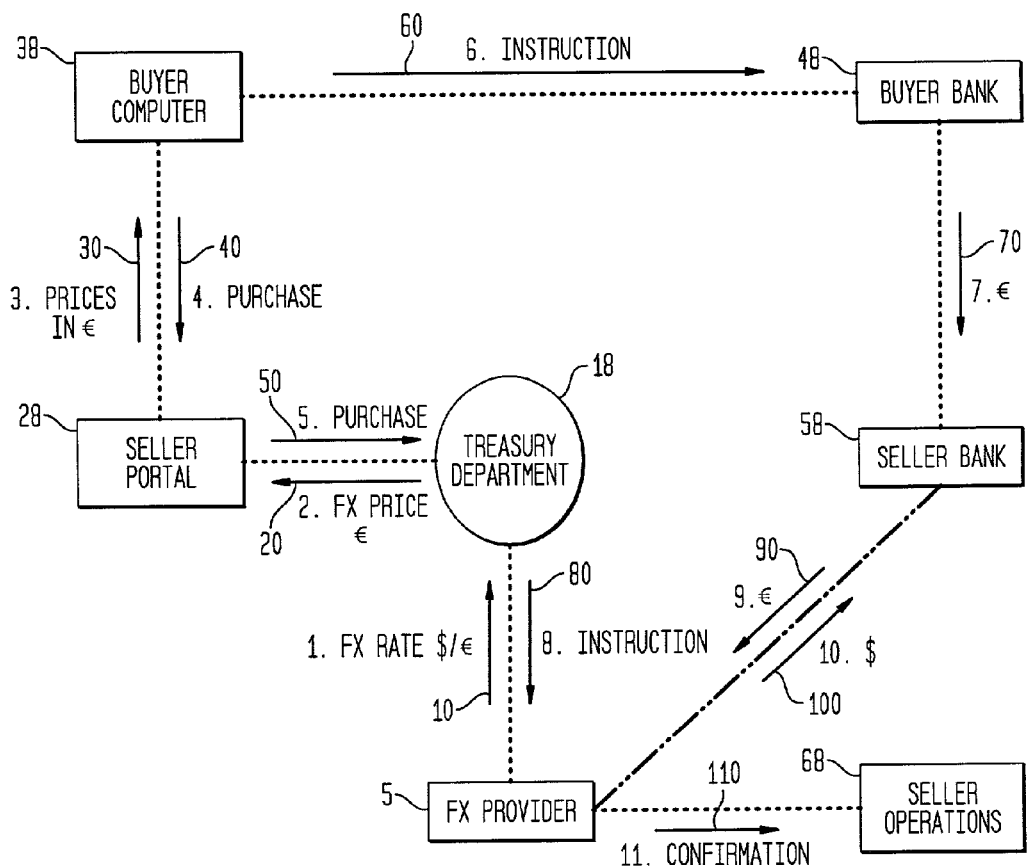
FIG. 1 schematically illustrates a conventional e-commerce and hedging transaction.
Figure 2:
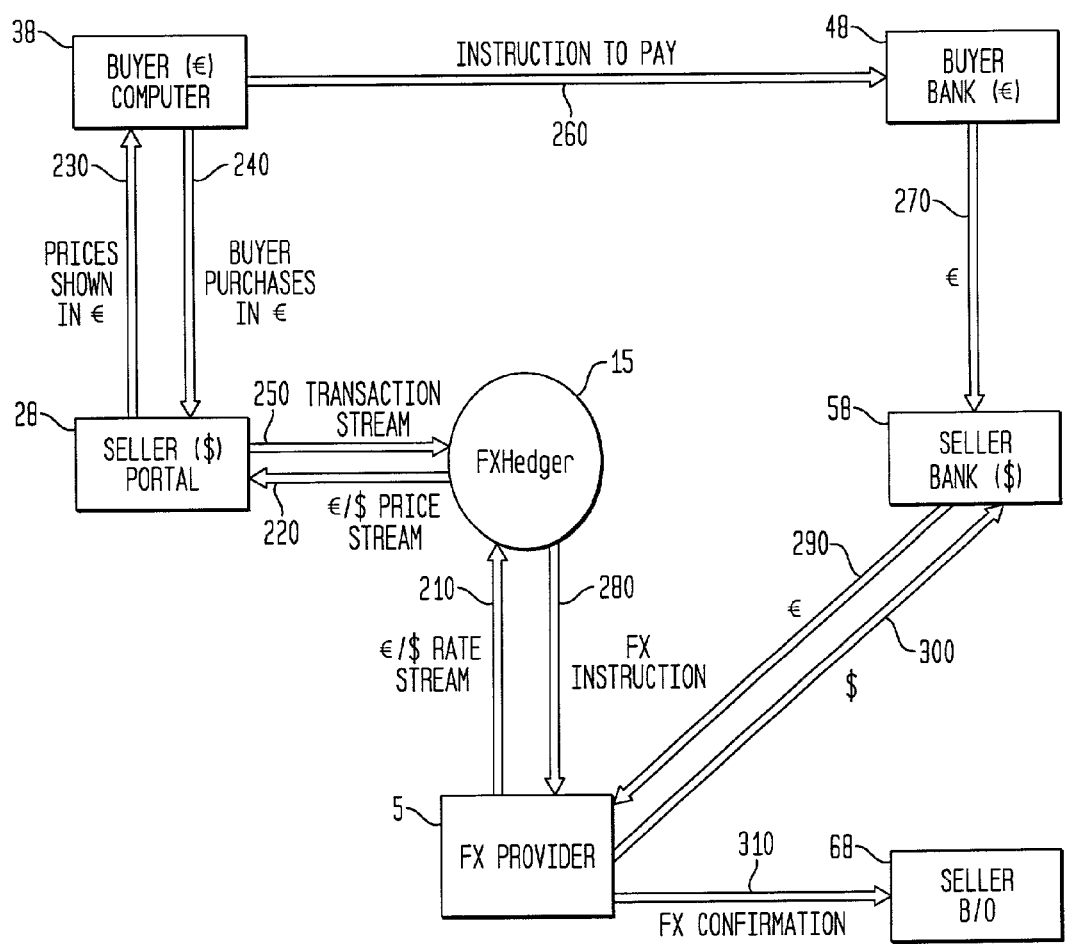
FIG. 2 schematically illustrates an embodiment of an automated e-commerce and hedging transaction, in accordance with the present invention.

FIG. 2 schematically illustrates an embodiment of the automated e-commerce and hedging transaction, in accordance with the present invention. As with FIG. 1, assume that S (seller of widgets) operates in currency $. B (buyer) operates in currency €. B goes to S's website to buy 1000 widgets. B only has a € bank account. S has a preferred FX rate provider 5 which offers €/$ trading capability. FX rate providers include, but are not limited to: 1) a multibank website that offers the customer access to multiple banks, such as Atriax, Currenex, and FXall; 2) a web service offering a live foreign exchange rate stream and an execution service at the published rates; and 3) the website of an individual bank offering live rates and execution capability. S also has a "nostro" bank 58, where S holds nostro accounts in both € and $. Again, assume at the time of the transaction, the foreign exchange is €1.1=$1.

In Step 210, S's chosen FX rate provider 5 streams market €/$ rates to the FX Hedger module 15. In Step 220, the FX hedger engine 15 adjusts the frequency and bid offer spread of the streamed €/$ prices and forwards the stream to S's portal (a website) 28, based on pricing rules discussed in detail below. In other words, the FX hedger transfers public price data streams to update the current foreign price of the goods. Portal 28 is preferably a business-to-business (B2B) portal which is a third-party website (e.g., an online marketplace, such as eSteel, Covisint, Converge, and PlasticsNet) or an individual customer's website, where the customer can buy or sell goods. A B2B portal may also be the buyer's website, where the seller can sell goods directly to the purchaser.

Returning to FIG. 2, S displays the prices of his widgets in €, at Step 230. Buyer B then purchases 1000 widgets at Step 240. In Step 250, the transaction record is passed, as a business transaction stream, to the FX hedger engine 15. In Step 260, B instructs his bank 48 to pay €1,100 to S's bank. B's bank 48 pays €1,100 to S's nostro bank 58 at Step 270. At this point, the FX hedger engine processes and aggregates this transaction with past transactions. If the thresholds or hedging criteria defined by S have been reached (based on received hedging rules), Steps 280 through 310 occur as follows.

In Step 280, an instruction is automatically sent from the FX hedger 15 to S's selected FX rate provider 5. The FX provider 5 then executes a foreign exchange transaction with S's nostro bank 58. Specifically, S's €account at nostro bank 58 pays €1,100 to FX provider 5 at Step 290. In Step 300, FX provider 5 pays $1,000 to S's $ account at nostro bank 58. Lastly, in Step 310, an FX confirmation is sent to S's operations department 68.

As compared to the prior art method of FIG. 1, the prices shown on S's website 28 reflect the current foreign exchange market, according to prescribed pricing rules captured in the FX hedger engine 15. The FX hedger engine provides a reliable, electronic audit of the FX hedging process. Specifically, it provides a tangible record to shareholders, management and regulators that appropriate hedging procedures have been followed. This is particularly important to assist in compliance with the new FAS (Financial Accounting Standards) 133 requirements.

The electronic linking of e-commerce website transaction data streams to the hedging activity provides closer association between the FX hedging activity and the underlying e-commerce activity. This enables better assessment of the efficiency and costs of the FX hedging activity. In addition, the customer's treasury department staff, shown in FIG. 1, may be reduced. Using the inventive hedging engine eliminates the manual intervention required to monitor and analyze the FX risk incurred as a consequence of the e-commerce activity. Equally, the task of sourcing FX rates and instructing execution have been automated by the hedging engine. As stated, the hedging engine may be hosted by a remote ASP that offers access to the hedging functionality, or directly at the customer's portal.

As described, the hedging engine receives both hedging and pricing rules from the customer. Hedging rules define when a hedging foreign exchange transaction should occur and how much should be exchanged. For example, the hedging rules may provide that hedging will occur: every week (or any duration); every n number of sales; every y currency units of sales; when the market foreign exchange rate moves x percent; when the average foreign exchange rate achieved through sales and hedging in a certain recent period deviates from the market foreign exchange rate by x percent; and when manually requested.

Further, the hedging rules may provide rules to always hedge total accumulated foreign revenue or deficit, to only hedge x percent of accumulated foreign revenue or deficit, or to hedge all accumulated foreign revenue/deficit but not if less than y foreign currency units. Of course, these are only examples of possible hedging rules and are not exhaustive.

Pricing rules define when and how much to update the foreign currency prices being used by the customer to buy or sell goods through their website or their associated B2B portals. In other words, they define when and how to update the foreign buying and selling prices. For example, the pricing rules may provide an updated public foreign exchange rate: every week (or any time duration); when market foreign exchange rate moves x amount or percent; when the rate used to determine the current public foreign exchange rate differs from the market foreign exchange rate by more than x amount or percent; and when manually requested.

In addition, pricing rules may update the foreign exchange rate, used to determine the foreign price of the goods, to equal the current market foreign exchange rate, or update the foreign exchange rate to equal the current market foreign exchange rate adjusted by a selected variable. The adjustment may be a simple increment/decrement or a percentage of the market rate. For example, one reason for adjusting the actual market rate is to protect the seller if the seller pricing rules updates the foreign exchange rate once a month (which is a relatively long duration). Therefore, the seller decides to "mark up" the foreign exchange rate by 5 or 10% to "hedge" against a potential drop in the foreign exchange rate over the month.

To illustrate hedging and pricing rules, consider the following example. Assume that a U.S. based customer, who manufactures and sells goods in Europe, wishes to receive remuneration in U.S. currency. The foreign exchange rate (EURUSD fx rate), as received from the customer's FX provider is the number of U.S. dollars (USD) that is equal to 1=€(EUR). Let us also assume that the customer has set the pricing and hedging rules as follows:

Pricing
a) set selling price=price in USD/(0.95*EURUSD fx rate)
b) update selling price whenever EURUSD fx rate has moved +2% or −2% from the last update Hedging
a) when sales in EUR reach 100,000 EUR, sell accumulated EUR revenues, and buy USD at the prevailing exchange rate.
b) if the EURUSD exchange rate has moved −2% since the last hedge, sell accumulated EUR revenues, and buy USD at the prevailing exchange rate.

Now consider a product that the customer wishes to sell for $30,000 USD. Below is a series of fluctuating EURUSD fx rates and sales, and the resulting hedge transactions:

Assume that the EURUSD & rate begins at 0.8
Pricing rule a) applies, so selling price is now calculated using fx=(0.8*0.95)=0.76
Assume customer sells 3 items, each at $30,000*3/0.76==€118,421 EUR
Hedging rule a) applies, and instruction is sent to the FX provider to sell €118,421
Since the EUR is at 0.8, $94,737 USD is realized, yielding a $4,737 foreign exchange profit
Now customer sells 2 items, each at $30,000*2/0.76==€78,947 EUR
Assume EURUSD FX rate lowers to 0.78
Pricing rule b) applies, so selling price now calculated using FX=(0.78*0.95)=0.741
Hedging rule b) applies, and instruction is sent to the FX provider to sell €78,947
Since the EUR is at 0.78, $61,579 USD is realized, yielding a $1,579 foreign exchange profit
Now customer sells 2 items, each at $30,000*2/0.741==€80,972 EUR
Assume EURUSD FX rate lowers to 0.76
Pricing rule b) applies, so selling price now calculated using fx=(0.76*0.95)=0.722
Hedge rule b) applies, and instruction is sent to the FX provider to sell €80,972
Since the EUR is at 0.76, $61,538 USD is realized, yielding a $1,538 foreign exchange profit
Assume EURUSD FX rate lowers to 0.75
Now customer sells 3 items, each at 30,000*3/0.722==€124,654 EUR
Hedging rule a) applies, and instruction is sent to the FX provider to sell €124,654
Since the EUR is at 0.75, $93,490 USD is realized, yielding a $3,490 FX profit In summary, for the above series, the total U.S. dollar sales equaled $300,000; however, the total U.S. dollar revenue equaled $311,345, yielding a total $11,345 foreign exchange profit. Compare this with the earlier Yahoo! example, which incurred a substantial foreign exchange loss.

FIG. 3 schematically illustrates another embodiment of the automated e-commerce and hedging transaction method. Specifically, FIG. 3 includes a customer 25, business-to-business portals 35, FX rate provider 5, and hedging engine 15. As will be described with reference to FIGS. 5A to 5I, hedging engine 15 may be hosted at an ASP, remote from the customer, or may reside on the customer's computer or local network.

FIG. 3 further illustrates the flow of the hedging and underlying goods transactions through a series of 10 stages. Stage 1 transfers B2B transaction streams from B2B portals 35 to customer 25. Stage 2 transfers the received B2B transaction streams from customer 25 to hedging engine 15. Stage 3 transfers market foreign exchange rate streams from FX rate provider 5 to customer 25. Next, Stage 4 transfers the received market rate streams from customer 25 to hedging engine 15. Stage 5 transfers pricing rules from customer 25 to hedging engine 15. Similarly, Stage 6 transfers hedging rules from customer 25 to hedging engine 15. Stage 7 transfers public price streams (based on the received pricing rules) from the hedging engine 15 to customer 25. The customer 25 then transfers the public price streams to the B2B portals 35 at Stage 8. Stage 9 transfers hedge instruction streams (based on the received hedging rules) from hedging engine 15 to customer 25. Lastly, stage 10 transfers the received hedge instruction streams from customer 25 to FX portal 5.

FIG. 4 illustrates a similar transaction, compared to FIG. 3, with minor differences. For example, different B2B portals are shown separate as symbols 35A, 35B, and 35C. In Stages 1 and 2, the B2B transaction streams are transferred from the B2B portals directly to hedging engine 15 (as opposed to via the customer in FIG. 3). In Stage 4, market rate streams are transferred from FX rate provider 5 directly to the hedging engine. Further, public price streams are transferred, in Stage 8, from the hedging engine 15 directly to the B2B portals 35. Similarly, hedge instruction streams are transferred, in Stages 9 and 10, from the hedging engine 15 directly to the FX portal 5. These differences shown in FIG. 4 reduce the number of transactions verses FIG. 3. This will be explained in detail with reference to FIGS. 5A to 5I.

FIGS. 5A to 5I schematically illustrate the Stages of FIGS. 3 and 4. For each stage, different examples are illustrated, depending on the location of the hedging engine, as well as other factors described below. Further, each of FIGS. 5A to 5I are described independently in respect to one another.

Figure 5A:
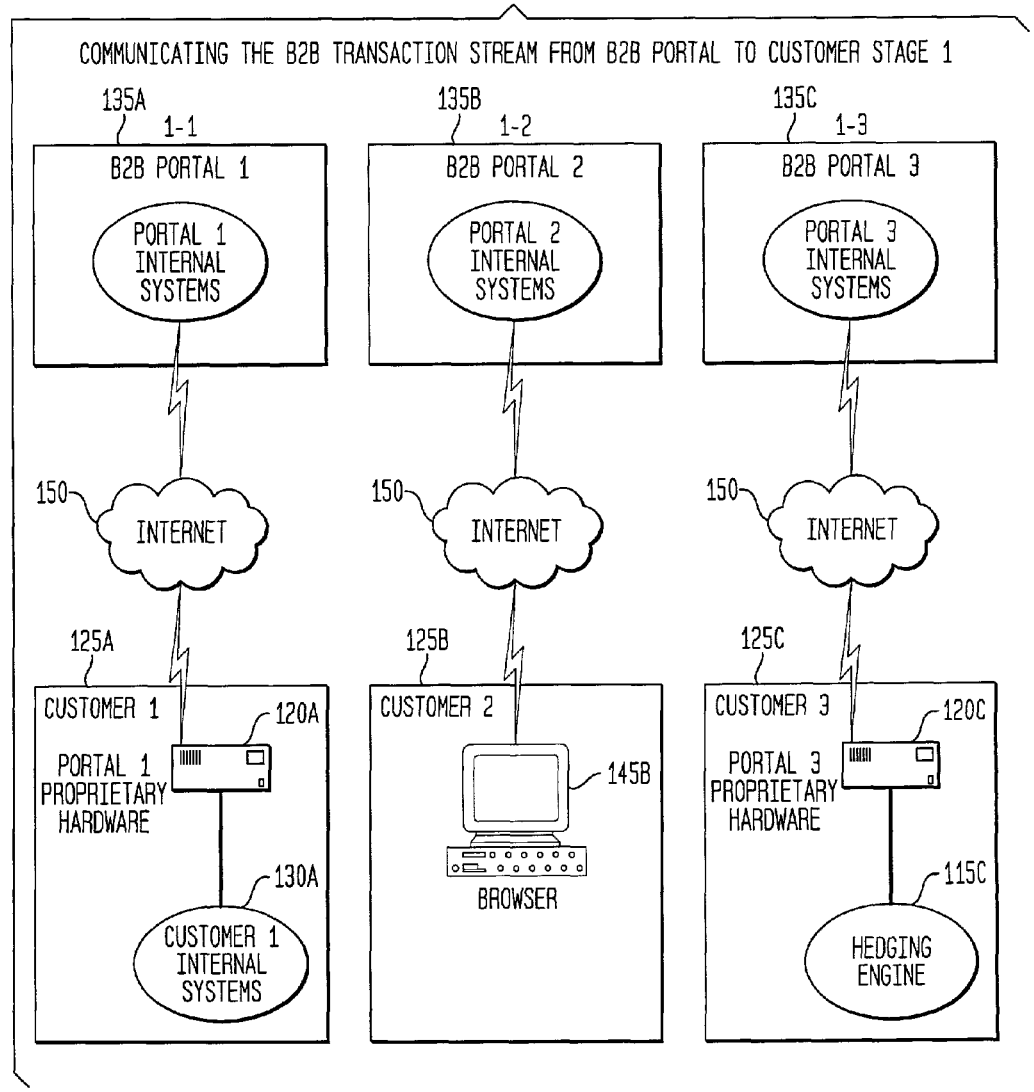

FIG. 5A illustrates three scenarios for Stage 1: 1-1, 1-2, and 1-3. Scenarios 1-1 and 1-2 are applicable to both ASP and non-ASP applications, while scenario 1-3 is only applicable to non-ASP applications. An ASP application is when the hedging engine resides on a remote server hosted by an ASP, and a non-ASP application is when the hedging engine resides with the customer.

In scenario 1-1, the customer 125A accepts the stream of B2B transactions into his internal systems 130A via an API 120A (as proprietary hardware of portal 135A) over the Internet 150. In scenario 1-2, the customer 125B accesses details of his B2B transactions via a browser window 145B that is connected to the B2B Portal 135B over the Internet 150. In scenario 1-3, the hedging engine 115C of customer 125C accepts the stream of B2B transactions via proprietary API 120C of portal 135C.

FIG. 5B illustrates five scenarios for Stage 2: 2-1, 2-2, 2-3, 2-4, and 2-5. Scenarios 2-1, 2-2, and 2-5 are applicable to ASP applications, while scenarios 2-3 and 2-4 are applicable to non-ASP applications. In scenario 2-1, customer 225A transfers details of his B2B transactions from browser window 235A to the hedging engine 215A residing in ASP 260A, over the Internet 150. In scenario 2-2, customer 225B transfers details of his B2B transactions from his internal systems 230B to the hedging engine 215B via an API 265B (as proprietary hardware of ASP 260B) over the Internet 150. As shown, hedging engine 215B resides in ASP 260B. In scenario 2-3, customer 225C inputs details of his B2B transactions into local hedging engine 215C via a terminal window 240C. In scenario 2-4, customer 225D transfers details of his B2B transactions from his internal computer systems 230D directly to local hedging engine 215D. Lastly, in scenario 2-5, customer 225E is completely bypassed (See also FIG. 4). Instead, a hedging engine 215E, via API 220E, accepts a stream of customer's 225E B2B transactions from B2B portal 235E. In fact, both Stages 1 and 2 are achieved in scenario 2-5 (FIG. 4).

Figure 5C:
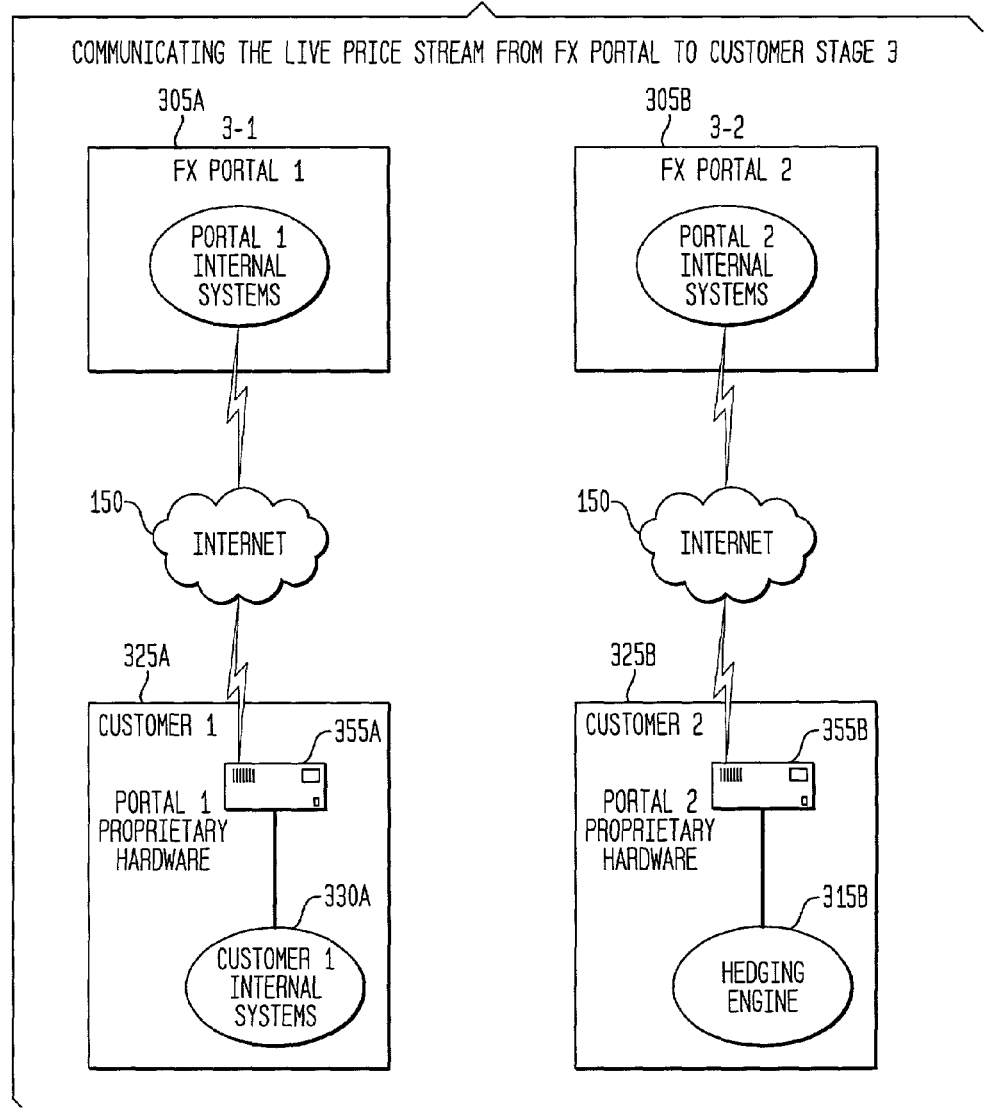

FIG. 5C illustrates two scenarios for Stage 3: 3-1 and 3-2. Scenario 3-1 is applicable to both ASP and non-ASP applications, while scenario 3-2 is applicable to non-ASP applications only. In scenario 3-1, customer 325A accepts streams of market foreign exchange prices into his internal computer systems 330A from an FX portal 305A via an API 355A (as proprietary hardware of FX portal 305A) over the Internet 150. In scenario 3-2, a hedging engine 315B accepts streams of market foreign exchange rates from an FX portal 305B via an API 355B (as proprietary hardware of FX portal 305B) over the Internet 150.

Figure 5D:
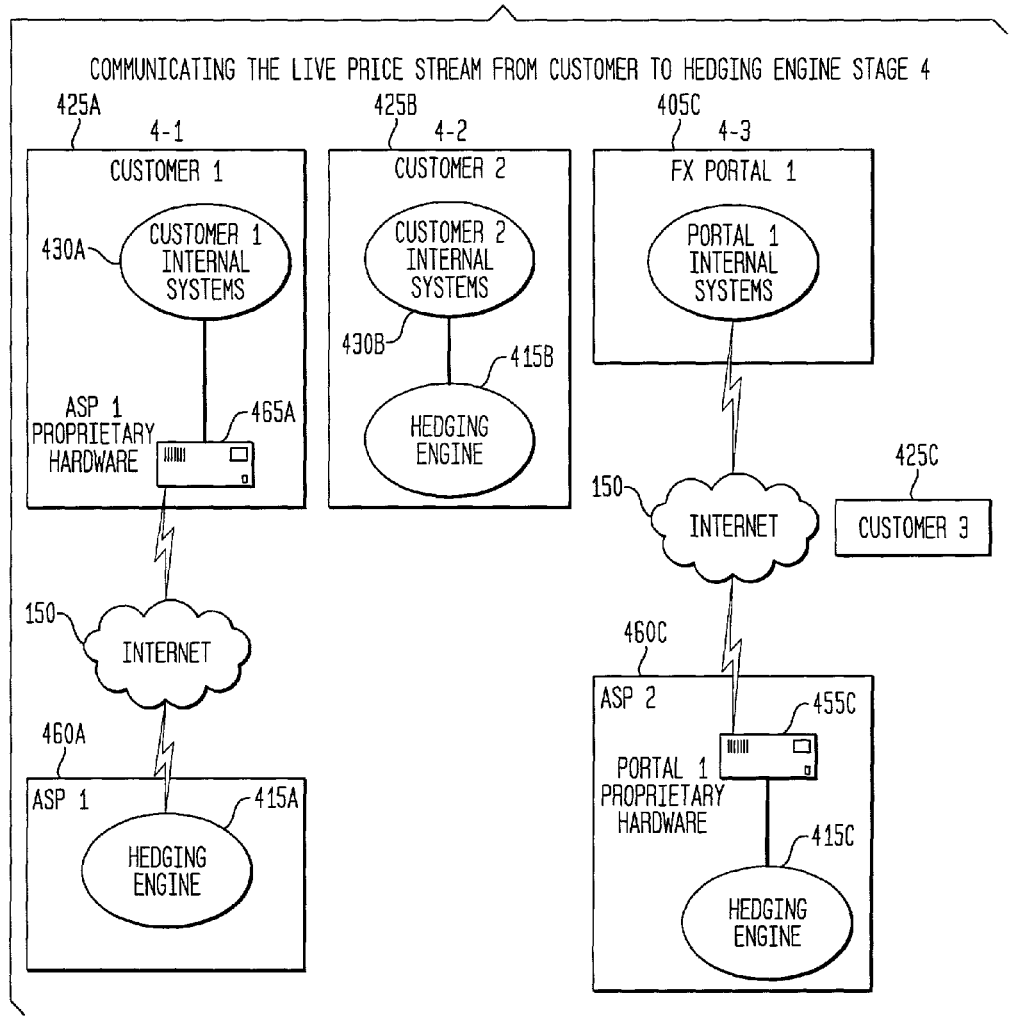

FIG. 5D illustrates three scenarios for Stage 4: 4-1, 4-2 and 4-3. Scenarios 4-1 and 4-3 are applicable to ASP applications, while scenario 4-2 is applicable to non-ASP applications. In scenario 4-1, streams of market foreign exchange rates are transferred from the internal systems 430A of a customer 425A to a hedging engine 415A, located in ASP 460A, via an API 465A (as proprietary hardware of FX portal 460A) over the Internet 150. In scenario 4-2, the market foreign exchange rates are transferred from the internal systems 430B of a customer 425B to the customer's hedging engine 415B. Lastly, in scenario 4-3, customer 425C is bypassed as shown (See also FIG. 4). Instead, a hedging engine 415E, via an API 455C (as proprietary hardware of FX portal 405C), accepts the market rate streams from FX portal 405C.

Figure 5E:
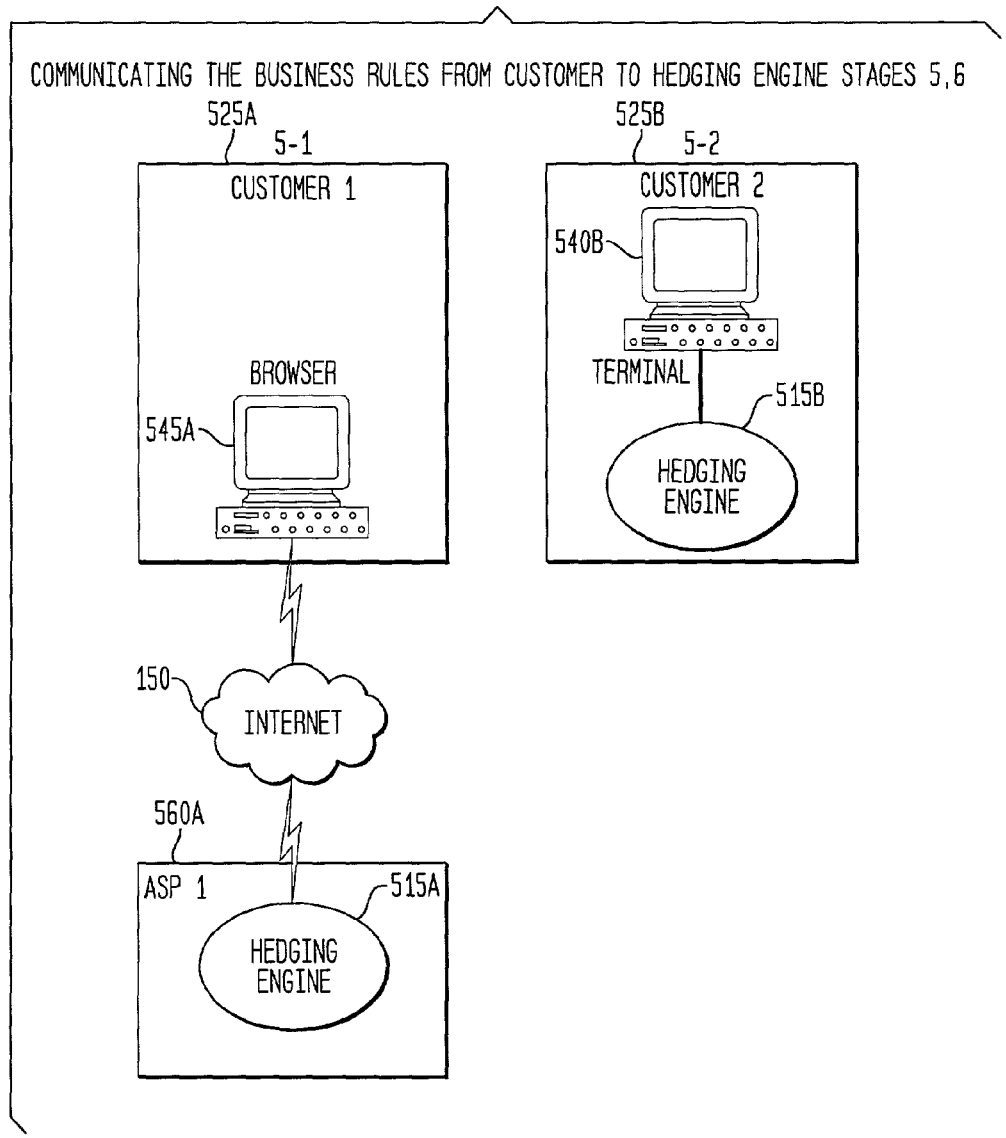

FIG. 5E illustrates two scenarios for Stages 5 and 6: 5-1 and 5-2. Scenario 5-1 is applicable to ASP applications, while scenario 5-2 is applicable to non-ASP applications. In scenario 5-1, both pricing and hedging rules are transferred, via the Internet 150, from a browser window 545A of customer 525A to a hedging engine 515A residing in ASP 560A. In scenario 5-2, both pricing and hedging rules are transferred from a terminal 540B of customer 525B to a hedging engine 515B residing at the customer 525B, as shown.

Figure 5F:
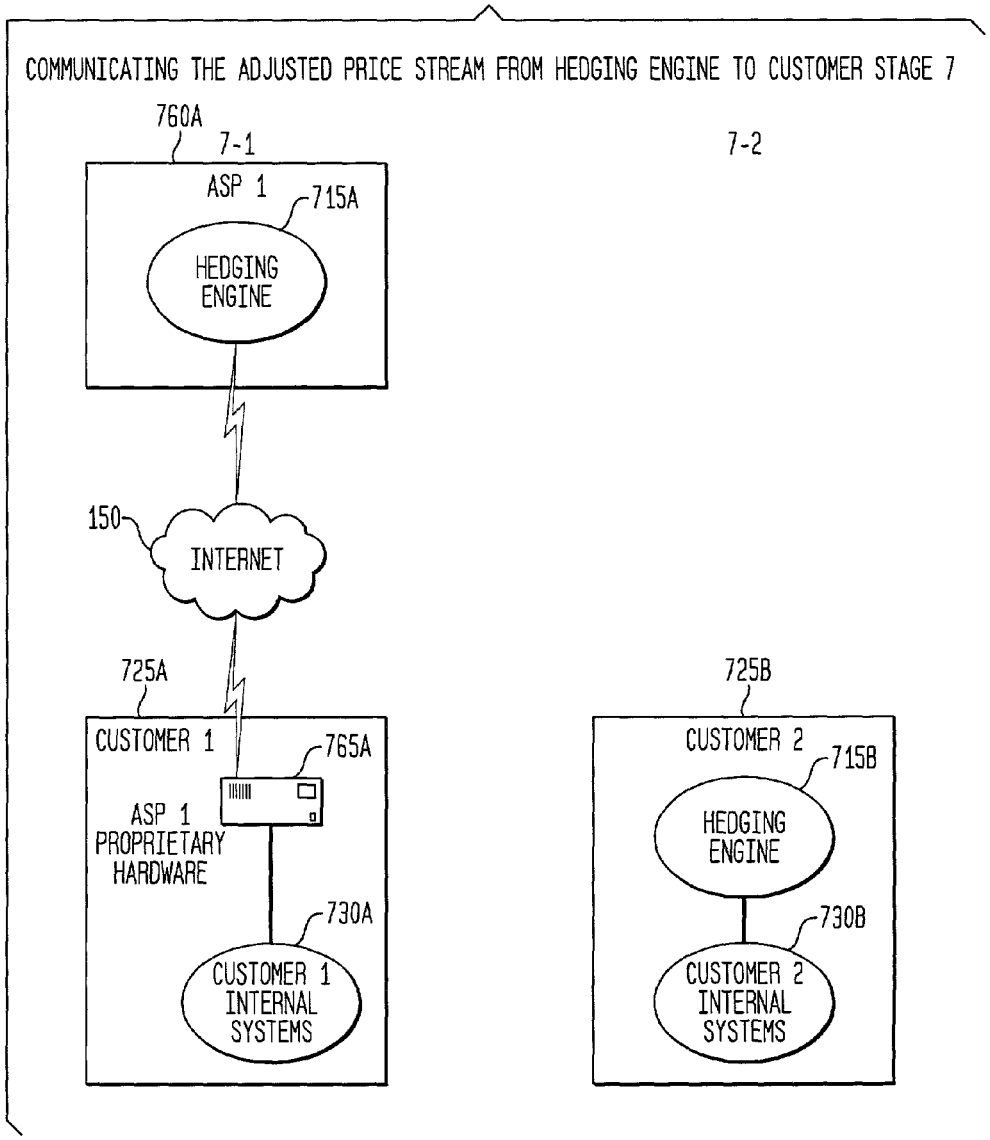

FIG. 5F illustrates two scenarios for Stage 7: 7-1 and 7-2. Scenario 7-1 is applicable to ASP applications, while scenario 7-2 is applicable to non-ASP applications. In scenario 7-1, the public price streams are transferred, over the Internet 150, from a hedging engine 715A residing in ASP 760A to the internal systems 730A of customer 725A via an API 765A (as proprietary hardware of ASP 760A). In scenario 7-2, the public price streams are transferred from a hedging engine 715B, residing in a customer 725B, to the customer's internal systems 730B.

FIG. 5G illustrates three scenarios for Stage 8: 8-1, 8-2 and 8-3. Scenario 8-1 is applicable to non-ASP applications, scenario 8-2 is applicable to both ASP and non-ASP applications, and scenario 8-3 is applicable to ASP applications. In scenario 8-1, the public price stream is transferred from the hedging engine 815A, residing in customer 825A, to a B2B portal 835A, via an API 820A (as proprietary hardware of B2B portal 835A) over the Internet 150. In scenario 8-2, the public price stream is transferred from the internal systems 830B of customer 825B to a B2B portal 835B, via an API 820B (as proprietary hardware of B2B portal 835B) over the Internet 150. Lastly, in scenario 8-3, customer 825C is bypassed as shown (See also FIG. 4). Instead, a hedging engine 815C residing in ASP 860C, via an API 820C (as proprietary hardware of B2B portal 835C), transfers the public price stream to B2B portal 835C over the Internet 150.

Figure 5H:
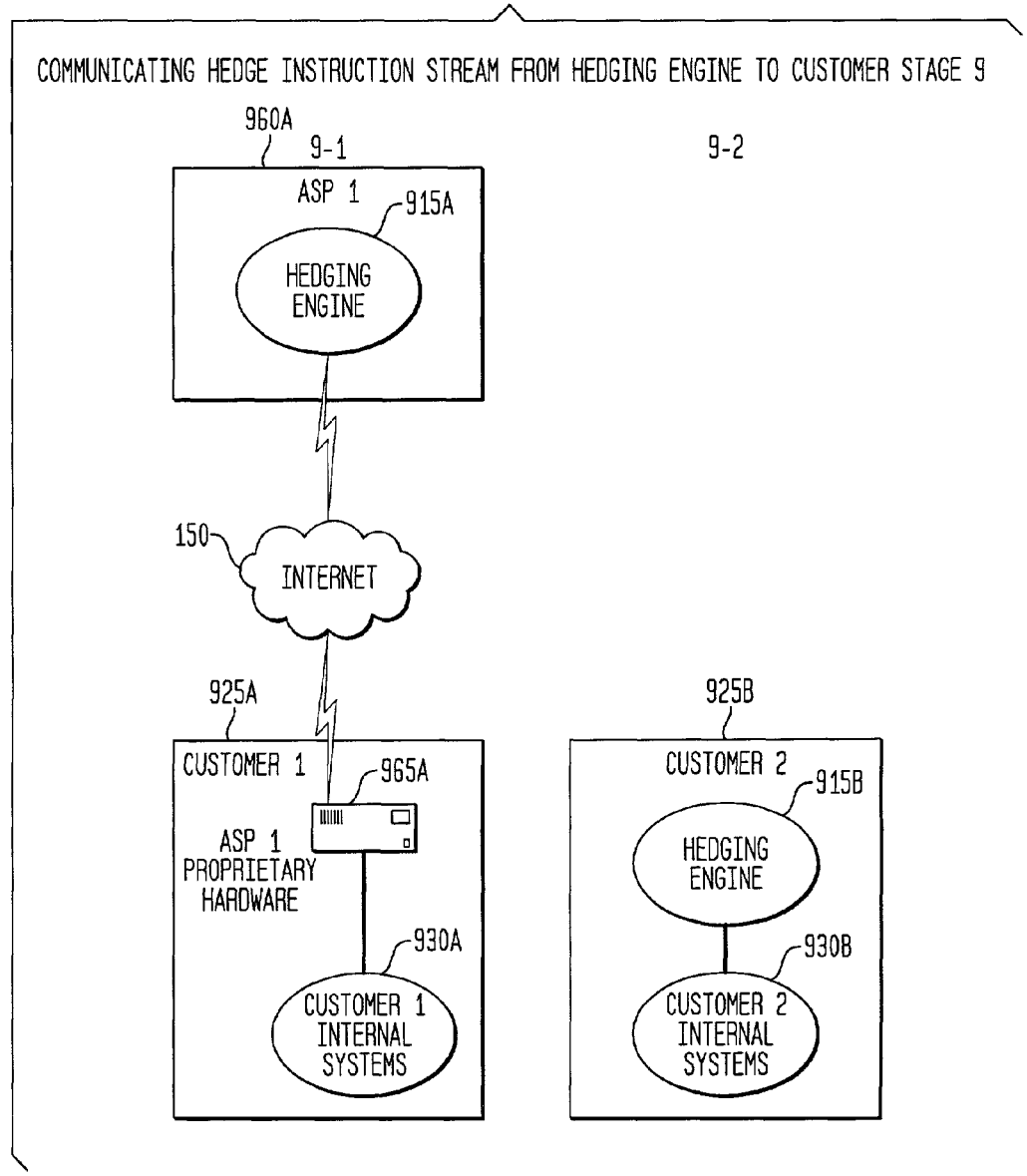

FIG. 5H illustrates two scenarios for Stage 9: 9-1 and 9-2. Scenario 9-1 is applicable to ASP applications, while scenario 9-2 is applicable to non-ASP applications. In scenario 9-1, the hedge instruction stream is transferred, over the Internet 150, from a hedging engine 915A residing in ASP 960A to the internal systems 930A of customer 925A via an API 965A (as proprietary hardware of ASP 960A). In scenario 9-2, the hedge instruction stream is transferred from a hedging engine 915B, residing in a customer 925B, to the customer's internal systems 930B.

FIG. 5I illustrates four scenarios for Stage 10: 10-1, 10-2, 10-3, and 10-4. Scenario 10-1 is applicable to non-ASP applications, scenarios 10-2 and 10-3 are applicable to both ASP and non-ASP applications, and scenario 10-4 is application to ASP applications. In scenario 10-1, customer 1025A transfers the hedge instruction stream from a hedging engine 1015A, via an ASP 1055A (as proprietary hardware of FX portal 1005A), to FX portal 1005A, over the Internet 150. In scenario 10-2, customer 1025B transfers the hedge instruction stream from its internal systems 1030B, via an ASP 1055B (as proprietary hardware of FX portal 1005B), to FX portal 1005B, over the Internet 150. In scenario 10-3, the hedge instruction stream is transferred from the browser 1045C of customer 1025C to FX portal 1005C, over the Internet 150. Lastly, in scenario 10-4, customer 1025D is bypassed (See also FIG. 4). Instead, a hedging engine 1015D residing in ASP 1060D, via API 1055D, transfers the hedging instructions to FX portal 1005D, over the Internet 150. In fact, both Stages 9 and 10 are achieved in scenario 10-4 (FIG. 4).

Figure 6:
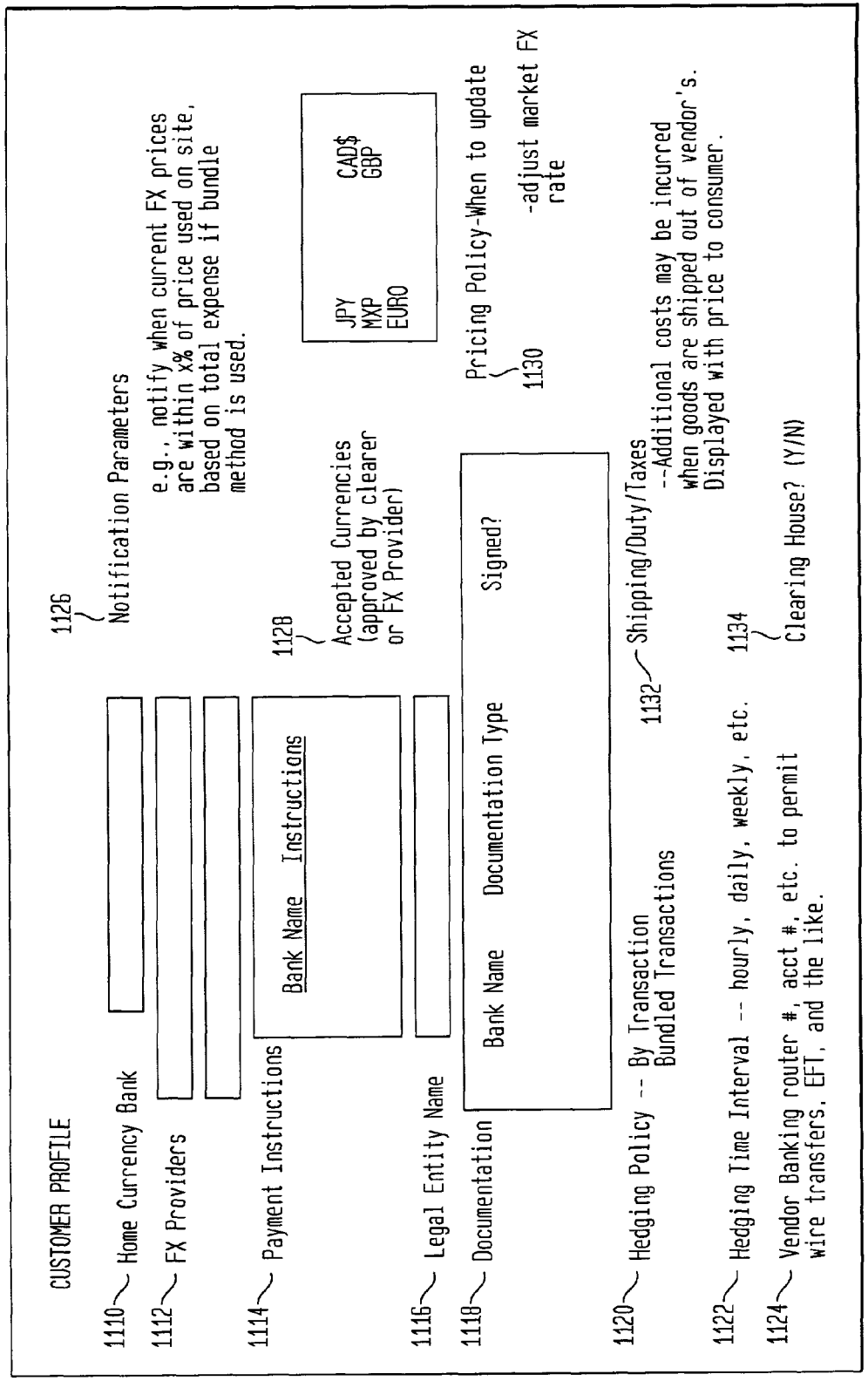
FIG. 6 illustrates a vendor profile, in accordance with the present invention.

The following is an example a business implementation of the inventive hedging engine. In this example, assume that an "e-Business solutions" Internet company (e-Company) implements the hedging engine (i.e., e-Company is the ASP which hosts the hedging engine). Illustratively, e-Company will offer the hedging engine to its customers. Each customer that wishes to participate will complete a customer profile form (typically online). FIG. 6 is an example of such a customer profile form. Of course, the form can greatly vary, requiring greater or less information.

As illustrated in FIG. 6, a customer will enter its home currency bank, line 1110, and current FX rate providers, line 1112, that it currently has or desires to have a credit relationship. On line 1134, the customer can select to use a clearing house. A clearing house typically has a subset of FX providers to select. On line 1114, the customer enters payment instructions regarding each bank. On line 1116, the customer enters its legal name. On line 1118, the customer enters documentation for each bank. On line 1124, the customer enters its bank routing and account numbers to accept wire payments. Hedging rules are entered on lines 1120 and 1122, and pricing rules are entered on line 1130. The customer enters notification parameters, line 1126, that may be set up, e.g., to notify the customer when the market FX rate moves a certain percent from the FX rate used to determine the price of the customer's goods. On line 1128, the customer selects the currencies that it accepts (based on approval by the customer's FX provider and/or clearing house). Lastly, in this example, the customer determines how they will handle variables, such as shipping, duty, and taxes.

After the customer profile is complete, e-Company forwards messages to all financial institutions involved, and receives necessary approvals from these financial institutions to enable the foreign exchange hedging and foreign exchange transactions to take place. Upon approval, a window or dialog box is created on the customer's website (or e-Company's site) having, e.g., a pull down menu of currencies. This allows a purchaser, using the customer's website, to display prices in any offered currency, or possibly multiple currencies, that the purchaser chooses.

Once a transaction is complete, the hedging engine creates an electronic ticket between the customer and its FX rate provider containing all of the foreign exchange transaction details necessary to hedge the transaction, based on the hedging rules (lines 1120, 1122). However, if the customer has more than one FX provider (determined by the streaming market rate received from each FX provider), then the best rate is chosen.

If the constant streaming price is "worse" than the price being used by the customer on the website, notification is sent to the customer (if the customer activated this function on line 1126) using any number of mediums (e.g., E-mail, beeper, electronic phone call, etc.). These notifications may also occur in warning stages, as set up by the customer.

Once the initial underlying transaction is complete, these details are forwarded (e.g., electronically) to both the customer and the purchaser (as well as to the clearing house or FX provider) with the intention to feed any systems set up by the customer and purchaser (i.e., accounting, inventory, etc.). This is done simultaneously, typically without any extra keystrokes, with the transmission of the electronic foreign exchange ticket (described above).

If a purchase has been made for a good or service and the customer has chosen to bundle these transactions until a threshold is reached (as defined in the customer profile), then an application (which can be either a stand-alone or imbedded in the portal on the customer side) is used to monitor the risk that is being accumulated. If the customer wants to hedge the transaction prior to the threshold being reached, the customer can do so by clicking on a "hedge" button in this application and the electronic ticket would be created between the FX provider and the customer.

Finally, it should be understood that the foregoing description and all embodiments described above are merely illustrative of the invention. Numerous alternative embodiments within the scope of the appended claims will be apparent to those of ordinary skill in the art.

What is claimed is:

1. A hedging processor for monitoring business transactions for goods of commerce of a customer in a first type of currency, comprising:

at least one input for receiving business transaction information regarding a plurality of business transactions including purchases or sales of goods by a customer, for receiving hedging rules from the customer and set by the customer, wherein said hedging rules define a first user-specified event to initiate an exchange of the customer's first type of currency to a second type of currency on the customer's behalf, for receiving pricing rules from the customer and set by the customer, wherein said pricing rules define a second user-specified event to update foreign currency prices of said goods, and for receiving public price information from at least one of a plurality of foreign exchange (FX) rate providers or FX liquidity providers; and a processor operably arranged with said at least one input, the processor containing a computer readable program code for generating hedging instruction information to provide instructions to at least one of the plurality of FX rate providers or FX liquidity providers to exchange said first type of currency to said second type of currency, based on said hedging rules and the occurrence of the first user specified event, and for generating public price information to provide updated foreign currency prices of said goods to the customer, based on said pricing rules.

2. The processor of claim 1, wherein said transaction information is received via at least one transaction data stream, wherein said public price information is generated as at least one price data stream, and wherein said hedging instruction information is generated as at least one hedging instruction data stream.

3. The processor of claim 1, wherein said at least one input further receives, from the plurality of FX rate providers or FX liquidity providers, market rate information having current market foreign exchange rates including rates for exchanging said first type of currency to said second type of currency, and vice-versa.

4. The processor of claim 3, wherein said public price information is further based on the received market rate information.

5. The processor of claim 4, wherein said market rate information is received via at least one market rate data stream.

6. The processor of claim 1, wherein said pricing rules further define when to update said foreign currency prices of said goods, based on at least one of when the current market rate fluctuates by at least a first predetermined amount, when the rate from the public price information deviates from the current market rate by at least a second predetermined amount, after the expiration of a predetermined time interval, or any combination thereof.

7. The processor of claim 6, wherein said pricing rules further define rules to update said foreign currency prices of said goods, based on either the actual current market rate or said actual current market rate adjusted by a predetermined amount.

8. The processor of claim 1, wherein said hedging rules further define when to exchange said first and second types of currency, based on at least one of when the current market rate deviates from the market rate information by at least a first predetermined percent, after the expiration of a predetermined time interval, after a predetermined amount of units of said goods are sold or purchased, after a predetermined amount of currency received from sales or due from purchases of said goods, or any combination thereof.

9. The processor of claim 8, wherein said hedging rules further define an amount to exchange said first and second types of currency, based on either a total accumulated revenue or deficit of said first type of currency or a predetermined percent of said total.

10. The processor of claim 1, wherein said processor is configured within at least one of a local network or a stand-alone computer of said customer.

11. The processor of claim 1, wherein said processor is configured within an application service provider, remote from said customer.

12. The processor of claim 1, further comprising at least one output, the at least one output operably arranged with the processor for forwarding at least one hedging instruction data stream to at least one of the plurality of FX rate providers or FX liquidity providers.

13. The processor of claim 12, wherein said market rate data stream is received from said FX rate provider of said customer.

14. The processor of claim 1, wherein the FX rate provider of the plurality of FX rate providers or FX liquidity providers includes a multi-bank, an individual bank, a non-bank offering a live market foreign exchange price stream and an exchange service based on said price stream, or any combination thereof.

15. The processor of claim 1, wherein business transaction information includes a transaction data stream received from a business-to-business (B2B) portal, wherein said B2B portal is a medium to allow said customer to buy or sell said goods.

16. The processor of claim 15, wherein said B2B portal is at least one of an online marketplace, a vendor, a purchaser, or any combination thereof.

17. The processor of claim 16, further comprising at least one output to forward hedge instruction data streams and the public price data streams as an electronic ticket to at least one of said customer, said FX rate provider, said B2B portal, or any combination thereof.

18. A hedging processor for monitoring business transactions for goods of commerce of a customer in a first type of currency, comprising:
    at least one input for receiving business transaction information from a customer regarding a plurality of business transactions including purchases or sales of goods, for receiving currency exchange rules from a customer and set by the customer, wherein the currency exchange rules define a customer-specified event to initiate an exchange of a first currency to a second currency for the customer, and for receiving public price information from at least one of a plurality of foreign exchange (FX) rate providers or FX liquidity providers; and
    a processor operably arranged with said at least one input, the processor containing a computer readable program code for generating public price information to provide foreign prices of said goods, based on at least one of a predetermined foreign exchange rate, and for generating currency exchange instruction information to provide instructions to at least one of the plurality of FX rate providers or FX liquidity providers to exchange said first currency to said second currency, based on said currency exchange rules and the occurrence of the user-specified event.

19. A computerized method for administering transactions involving goods of commerce with a plurality of currency types comprising the steps of:
    receiving, by a hedging processor, currency exchange rules from a customer and set by the customer, wherein said currency exchange rules define a first customer-specified event relating to the customer's transactions involving said goods in a first type of currency that triggers the hedging processor to initiate an exchange of said first type of currency to a second type of currency for the customer;
    generating, by the hedging processor, currency exchange instruction information to provide instructions to exchange said first type of currency to said second type of currency for the customer;
    receiving, by the hedging processor, transaction information concerning the customer's transactions involving said goods;
    upon the occurrence of said first customer-specified event, forwarding, by the hedging processor, the currency exchange instruction information to at least one of a plurality of foreign exchange (FX) rate providers based on said currency exchange rules.

20. The computerized method for administering transactions according to claim 19, further comprising the steps of:
    receiving, by the hedging processor, pricing rules from the customer and set by the customer, wherein said pricing rules define a second customer-specified event that triggers the hedging processor to provide updated pricing of said goods in at least one of said first type of currency and said second type of currency based upon public price information provided by at least one of the plurality of FX rate providers;

upon the occurrence of the second customer user-specified event, receiving, by the hedging processor, updated pricing information of said goods from at least one of the plurality of FX rate providers based on said pricing rules.

21. The computerized method for administering transactions according to claim 20, wherein said transaction information is received via at least one transaction data stream, wherein said updated pricing information is received as at least one price data stream, and wherein said currency exchange instruction information is generated as at least one currency exchange instruction data stream.

22. The computerized method for administering transactions according to claim 21, further comprising the step of receiving, from one of the plurality of FX rate providers or a foreign exchange liquidity provider, market rate information having current market foreign exchange rates, including rates for exchanging said first type of currency to said second type of currency, and vice-versa.

23. The computerized method for administering transactions according to claim 22, wherein said step of generating said updated pricing information is further based on the received market rate information.

24. The computerized method for administering transactions according to claim 23, wherein said market rate information is received via at least one market rate data stream.

25. The computerized method for administering transactions according to claim 23, wherein said pricing rules further define when to update said foreign currency prices of said goods, based on at least one of when the current market rate fluctuates by at least a first predetermined amount, when the rate from the public price information deviates from the current market rate by at least a second predetermined amount, after the expiration of a predetermined time interval, or any combination thereof.

26. The computerized method for administering transactions according to claim 25, wherein said pricing rules further define rules to update said foreign currency prices of said goods, based on either the actual current market rate or said actual current market rate adjusted by a predetermined amount.

27. The computerized method for administering transactions according to claim 20, wherein said currency exchange rules further define when to exchange said first and second types of currency, based on at least one of when the current market rate deviates from the market rate information by at least a first predetermined percent, after the expiration of a predetermined time interval, after a predetermined amount of units of said goods are sold or purchased, after a predetermined amount of currency received from sales or due from purchases of said goods, or any combination thereof.

28. The computerized method for administering transactions according to claim 27, wherein said currency exchanging rules further define an amount to exchange said first and second types of currency, based on either a total accumulated revenue or deficit of said first type of currency or a predetermined percent of said total.

29. The computerized method for administering transactions according to claim 24, further comprising the steps of: forwarding said at least one currency exchanging instruction data stream to a foreign exchange (FX) rate provider of said customer.

30. The computerized method for administering transactions according to claim 29, wherein said market rate data stream is received from said FX rate provider of said customer.

31. The computerized method for administering transactions according to claim 29, wherein the plurality of FX rate providers include a multi-bank, an individual bank, a non-bank offering a live market foreign exchange rate stream and an exchange service based on said price stream, or any combination thereof.

32. The computerized method for administering transactions according to claim 30, wherein said transaction data stream is received from a business-to-business (B2B) portal, wherein said B2B portal is a medium to allow said customer to buy or sell said goods.

33. The computerized method for administering transactions according to claim 32, wherein said B2B portal is at least one of an online marketplace, a vendor, a purchaser, or any combination thereof.

34. The computerized method for administering transactions according to claim 33, further comprising the step of forwarding the currency exchange instruction data streams and the public price data streams as an electronic ticket to at least one of said customer, said foreign exchange rate provider, said B2B portal, or any combination thereof.

35. A computerized method for monitoring business transactions to provide foreign currency exchange hedging instructions and to provide foreign currency price information for goods of commerce, comprising the steps of:

receiving, by a hedging processor, hedging rules sent and set by a customer, the hedging rules defining a customer-specified event that triggers the hedging processor to initiate an exchange of the customer's first type of currency to a second type of currency;

generating, by the hedging processor, public price information to provide foreign prices of said goods, based on at least one of a predetermined foreign exchange rate received from at least one of a plurality of foreign exchange (FX) rate providers;

generating, by the hedging processor, hedging instruction information to provide instructions based on said hedging rules to exchange said first type of currency to said second type of currency; and receiving, by the hedging processor, transaction information concerning the customer's transactions involving said goods;

upon the occurrence of the user-specified event, transmitting, by the hedging processor, the hedging instruction information to those designated in said hedging rules.

* * * * *